(12) United States Patent
Shao et al.

(10) Patent No.: US 9,849,168 B2
(45) Date of Patent: Dec. 26, 2017

(54) ATTENUATED LIVE VACCINE AGAINST MYCOPLASMAL PNEUMONIA OF SWINE (MPS) AND USE THEREOF

(71) Applicant: JIANGSU ACADEMY OF AGRICULTURAL SCIENCES, Nanjing, Jiangsu (CN)

(72) Inventors: Guoqinq Shao, Nanjing (CN); Qiyan Xiong, Nanjing (CN); Maojun Liu, Nanjing (CN); Zhixin Feng, Nanjing (CN); Yanna Wei, Nanjing (CN); Haiyan Wang, Nanjing (CN); Fangfang Bai, Nanjing (CN); Yuan Gan, Nanjing (CN); Li Wang, Nanjing (CN); Daohua Zhang, Nanjing (CN); Dongxia Liu, Nanjing (CN); Lizhong Hua, Nanjing (CN); Yuzi Wu, Nanjing (CN); Yun Bai, Nanjing (CN); Zhanwei Wang, Nanjing (CN)

(73) Assignee: JIANGSU ACADEMY OF AGRICULTURAL SCIENCES, Nanjing (CN)

(*) Notice: Subject to any disclaimer, the term of this patent is extended or adjusted under 35 U.S.C. 154(b) by 0 days.

(21) Appl. No.: 15/113,909

(22) PCT Filed: Jan. 26, 2014

(86) PCT No.: PCT/CN2014/071506
§ 371 (c)(1),
(2) Date: Jul. 25, 2016

(87) PCT Pub. No.: WO2015/109578
PCT Pub. Date: Jul. 30, 2015

(65) Prior Publication Data
US 2016/0346372 A1 Dec. 1, 2016

(51) Int. Cl.
*C12Q 1/68* (2006.01)
*A61K 39/02* (2006.01)
*C12R 1/35* (2006.01)
*A61K 39/00* (2006.01)

(52) U.S. Cl.
CPC ............ *A61K 39/0241* (2013.01); *C12R 1/35* (2013.01); *A61K 2039/522* (2013.01); *A61K 2039/552* (2013.01); *A61K 2039/70* (2013.01)

(58) Field of Classification Search
CPC . A61K 39/04; C12N 1/20; C12Q 1/02; C12Q 1/26; C12Q 1/32; C12Q 1/68
See application file for complete search history.

(56) References Cited

U.S. PATENT DOCUMENTS

| | | | |
|---|---|---|---|
| 2009/0068231 | A1 | 3/2009 | Kumar et al. |
| 2012/0045476 | A1 | 2/2012 | Kumar et al. |

FOREIGN PATENT DOCUMENTS

| | | | |
|---|---|---|---|
| CN | 86108515 | A | 10/1987 |
| CN | 1244580 | A | 2/2000 |
| CN | 101820902 | A | 9/2010 |
| CN | 103740625 | A | 4/2014 |

OTHER PUBLICATIONS

Oct. 10, 2014 International Search Report issued in International Patent Application No. PCT/CN2014/071506.

Primary Examiner — Jana A Hines
(74) Attorney, Agent, or Firm — Oliff PLC

(57) ABSTRACT

Disclosed are an attenuated live vaccine against mycoplasmal pneumonia of swine (MPS) and use thereof. In the present invention, pathological lung tissues of swine having typical *Mycoplasma hyopneumoniae* (Mhp) infection and no obvious other pathogenic infections are screened, and subcultured 100 generations in lungs of newborn rabbits; then, Mhp strains are isolated and serially subcultured in a medium; and the Mhp strain AN306 is obtained by screening a plurality of strains, which is deposited with an accession number: CCTCC NO. M2012431. Also disclosed is a live vaccine formulation against MPS prepared on the basis of the attenuated strain and comprising live attenuated strain, a pharmaceutically acceptable carrier or excipient, and optionally an adjuvant and immunogens of other pathogens.

11 Claims, No Drawings

ATTENUATED LIVE VACCINE AGAINST MYCOPLASMAL PNEUMONIA OF SWINE (MPS) AND USE THEREOF

BACKGROUND

Technical Field

The present invention relates to an attenuated vaccine strain against mycoplasmal pneumonia of swine (MPS), a live vaccine containing the attenuated strain, and use thereof in the protection against *Mycoplasma hyopneumoniae* (Mhp) infection related diseases.

Related Art

Mycoplasmal pneumonia of swine (MPS), common name pig asthma, is an infectious chronic respiratory disease of swine caused by Mhp, and the symptoms mainly include cough and shortness of breath. The disease mainly leads to decreased feed conversion rate and retarded growth of swine, and is characterized by high incidence and low mortality. MPS is highly prevalent worldwide, and brings about heavy economic losses to the modern swine industry.

Mhp generally forms, together with other pathogens, mixed infections. For example, swine enzootic pneumonia is induced by mixed infections with *Pasteurella Multocida*, *Streptococcus Suis* (SS), *Haemophilus Parasuis* of Swine (HPS), or *Actinobacillus Pleuropneumonia* of Porcine (APP). When mixed infections are caused by Mhp and Porcine Reproductive and Respiratory Syndrome Virus (PRRSV), Porcine Circovirus Type 2 (PCV2) and/or Swine Influenza Virus (SIV), common Porcine Respiratory Disease Complex (PRDC) takes places, which in turn causes not only respiratory system diseases, but also a decreased reproductive ability of the swine.

MPS is a refractory chronic infectious disease for which the therapeutic effect is less desirable, and that may easily reoccur after drug withdrawal and is difficult to be eradicated once it is epidemic in the pig farm. Therefore, the prevention, control and elimination of MPS are accomplished by means of comprehensive measures such as early diagnosis, timely isolation, antibiotic treatment or removal of affected pigs, vaccine prevention, all in and all out, and strict disinfection, where vaccine prevention plays a critical role in the control of MPS.

Although inactivated vaccines for MPS are currently massively used in clinic, the control effect for this disease is unsatisfactory. Moreover, the inactivated vaccines generally can lower the disease index of the lung of the affected pigs to some extent, but cannot decrease the proportion of diseased pigs effectively. MPS is accordingly considered as one of the infectious diseases of swine that are most widely epidemic, and most difficult to be eliminated. The poor effect of the vaccines may be attributed to the nature of the inactivated vaccines and the characteristics of Mhp infection.

Mhp binds to and is colonized on the bronchial ciliated epithelial cells through respiratory infection, thus causing persistent infection. After immunization with inactivated vaccines, systemic immune response is elicited; however, the local immune response inducing effect is poor. The circulating antibody produced needs to penetrate through the epithelium barrier, and be secreted into the tracheobronchial lumen. The process is quite difficult and suffers from low efficiency. For the purpose of effective immunization, the vaccine is required to stimulate the immune system to respond at a high level. Definitely, this necessitates relatively high dose of antigen and potent adjuvant, which lead to increased cost of the vaccine. Meanwhile, it is difficult to achieve the desirable control for the disease, because the immune response elicited by the inactivated vaccine can only inhibit the proliferation after infection with field strain and alleviate the tissue destruction, and cannot prevent the infection with field strain totally.

SUMMARY

An object of the present invention is to provide an attenuated live vaccine against MPS, which is useful in the prevention and control of diseases caused by Mhp infection, including diseases caused by co-infection with Mhp and other pathogens.

The attenuated live vaccine against MPS has a mechanism of action that is different from that of an inactivated vaccine, because after vaccination, the live vaccine strain proliferates in vivo to effectively activate the immune system in an organism, and is colonized on the bronchial ciliated epithelial cells after entering the respiratory system, to produce an "occupation effect", so that the field strain cannot be colonized, and the infection with the field strain may be blocked virtually, thus having a good anti-infective effect. Moreover, because the live vaccine strain can proliferate in vivo to effectively activate the immune system, the required dose is far lower than that of the inactivated vaccine. Therefore, the present invention is obviously advantageous over the inactivated vaccine in terms of the cost control, thereby facilitating the saving of social resources.

It is critical in the development of a live vaccine to obtain a highly immunogenic strain and an attenuation technology that decreases the virulence of the strain while the immunogenicity is maintained during attenuation.

According to the characteristics of the strain, an attenuation method in which the strain is subcultured 100 generations in newborn rabbits, and then subcultured in a cell free medium after 100 generations is employed in the present invention. The method has the advantage of in-vivo subculture in animals during the early subculture process, so as to avoid the defect of excessively rapid attenuation of the strain in an early stage caused by in-vitro subculture in a medium, which is detrimental to the maintenance of immunogenicity. The strain is subcultured in a cell free medium in a later stage, which facilitates the decrease in the number of attenuated generations to some extent, and the shortening of the attenuation process.

The strain is derived specifically by screening pathological lung tissues of swine having typical Mhp infection and no obvious other pathogenic infections, subculturing 100 generations in lungs of newborn rabbits, then isolating Mhp strains, and serially subculturing in a medium, and screening a plurality of strains. The strain screened out is designated as attenuated Mhp strain AN306. After attenuation by long-term multiple times of subculture, the attenuated strain losses the pathogenicity, is safe to the animals, and retains good immunogenicity, thus providing immunoprotection for immunized animals and preventing the occurrence of Mhp infection related diseases. It is confirmed through five-generation virulence recovery test that the attenuated strain AN306 will not be back mutated to a pathogenic virulent strain. Therefore, the attenuated strain AN306 is useful in the preparation of vaccines or multi-valent vaccines against MPS.

The attenuated Mhp strain was deposited on Oct. 25, 2012, in China Center for Type Culture Collection (CCTCC) (University, 299 Bayi Road, Wuchang, Wuhan, Luojiashan 430072, CHINA) with an accession number: CCTCC NO. M2012431.

Another object of the present invention is to disclose an attenuated live vaccine against MPS, which may be a vaccine or multi-valent vaccine against MPS, and comprises the attenuated Mhp strain AN306, and a pharmaceutically acceptable carrier or excipient. The carrier or excipient mainly includes three classes of substances, which may be varied depending on the particular use and immunization route of the vaccine. One class includes a solvent or a buffer system, including sterile physiological saline and sterile phosphate buffer; one class includes a lyoprotectant, including skimmed milk powder, gelatine, and sucrose, which is added to the lyophilized system when the vaccine is prepared to have a lyophilized form, to help in the maintenance of the activity of the live vaccine; and one class includes a spray protectant, mainly including glycerol, which is added when the live vaccine is used by aerosol immunization, to help in the maintenance of the activity of the live vaccine during spraying.

Furthermore, the live vaccine formulation against MPS according to the present invention may further contain an immunization adjuvant.

Adjuvant is an ingredient commonly used in vaccines for enhancing the immunostimulatory potency of the vaccines. The adjuvant useful in the present invention is a suitable adjuvant for the live vaccine against MPS that meets the requirements for immunization against MPS without obviously compromising the viability of the live vaccine.

The immunization adjuvant disclosed in the present invention may be a single adjuvant ingredient or a combination of two or more adjuvant ingredients. The adjuvant ingredient may include one or more of Chinese herbal medicine polysaccharides, carbomers, chitosan, immunostimulating complex matrix, levamisole, dextran, CpG, and bursin. The mixing ratio and dosage of various immunization adjuvant ingredients vary depending on the specific dosage and route of administration of the live vaccines.

The live vaccine formulation against MPS according to the present invention may further contain an immunogen of at least an additional pathogen, to form a multivalent vaccine for use. The additional pathogen includes at least one of viruses, bacteria, fungi, and parasites, for example, porcine circovirus, *Haemophilus parasuis*, porcine reproductive and respiratory syndrome virus, *Mycoplasma hyorhinis*, swine mycoplasmal *hyosynoviae*, porcine influenza virus, and others. These pathogens frequently clinically form, in respiratory tract, mixed infections with or infections secondary to Mhp, and contribute to each other, causing the disease to exacerbate and bringing about a great risk to the health of the swine. Therefore, when the vaccines against these pathogens are used in combination with the live vaccine against MPS, the mixed infections of Mhp and other pathogens can be prevented. The immunogens of other pathogens may be in the form of live or inactivated bacteria or viruses, or in the form of protein subunits. It should be noted that the carrier, excipient, and adjuvant used in the vaccines against other pathogens need to be compatible with the system of, and tolerable by the present live vaccine against MPS.

Immunization may be conducted with the attenuated live vaccine against MPS according to the present invention through various routes, including intrapulmonary injection, intramuscular injection, aerosol immunization, oral immunization, and nasal immunization. The attenuated live vaccine may be in the form of an intrapulmonary injectable formulation, an intramuscular injectable formulation, an aerosol, an oral formulation or a nasal drop. The route of immunization is selected depending on the animal being vaccinated, the vaccination history, the environment in the pig farm, and the convenience in operation of the person administering the vaccine. After an organism is infected with Mhp, Mhp initially binds to the bronchial ciliated epithelial cells in the lung to cause the cilium to fall off, then further invades the tissue to induce inflammation, and opens an access to infection with other pathogens. When the immunization is carried out with the live vaccine against MPS by intrapulmonary injection, the live vaccine may be directly injected into the target tissue, bind to the ciliated cells, and occupy the binding site, thereby preventing the infection with the field strain. When the immunization is carried out with the live vaccine against MPS through aerosol immunization, the live vaccine is enabled to reach the lower respiratory tract of the animal by controlling the size of the droplets, and effectively binds to the bronchial ciliated epithelial cells. Moreover, the workers needed for immunization are reduced by the use of vaccines as aerosol in a closed livestock shed or space. Intramuscular injection is a common route for immunization of animals, which is convenient and highly acceptable. When the immunization is carried out with the live vaccine against MPS by intramuscular injection, the animals are induced to produce systemic humoral and cellular immune responses, and the infection with the Mhp field strain is inhibited by the immune response mapping to the local target lung tissue. When the live vaccine against MPS is inoculated by oral or nasal immunization, the local mucosal immune response of intestinal tract or nasal cavity is induced, and the lymphocytes are nested to different mucosal site by means of the common mucosal immune system, thereby eliciting the immune response of the bronchial lung tissue in the lower respiratory tract, and achieving the protection against infection with Mhp field strain. Depending on the route of inoculation employed, the immunization adjuvant used may be varied. Therefore, the attenuated live vaccine against MPS according to the present invention is useful in the prevention and treatment of Mhp infection related diseases. The attenuated live vaccine against MPS according to the present invention is prepared by combining the attenuated Mhp strain AN306 with a pharmaceutically acceptable carrier or excipient, at least an immunization adjuvant, and an immunogen of at least an additional pathogen.

The live vaccine against MPS according to the present invention may be inoculated in either a single, or two or more repeated immunizations to enhance the immune response, which may be specifically determined depending on the route of immunization and the conditions of the animals. The time for single immunization is generally at an age of 3-10 days, and preferably 5-7 days. The time for the first immunization of 2 or more repeated immunizations is generally at an age of 3-10 days, and preferably 5-7 days. The interval between two immunizations is generally 2-3 weeks.

Matter Relating to Deposit of Sample of Biological Material

The attenuated Mhp strain AN306 was designated as Mhp AN306, and deposited on Oct. 25, 2012, in China Center for Type Culture Collection (CCTCC) (Wuhan University, 299 Bayi Road, Wuchang, Wuhan, Luojiashan 430072, CHINA) with an accession number: CCTCC NO. M2012431.

DETAILED DESCRIPTION

The present invention is further described and discussed with reference to specific embodiments; however, the present invention is not limited thereto.

For the purpose of illustrating the screening, subculture, and identification of the live vaccine strain against MPS according to the present invention as well as the immunogenicity and safety of the live vaccine strain, and confirming that by using the live vaccine formulations against MPS according to the present invention that are inoculated through various routes of immunization and contain various adjuvants and immunogens of additional different pathogens, the Mhp infection can be effectively prevented and the incidence of MPS can be controlled, the following experiments and preparations are conducted.

Example 1: Acquisition of Mhp AN306

Acquisition of Virulent Strain:

In 1975, Jiangsu Academy of Agricultural Sciences carried out the screening of virulent and pathogenic Mhp strains by collecting the typical MPS affected tissue samples from agricultural universities and national and provincial academy of science in more than 20 provinces all over the country, according to the requirements of the Ministry of agriculture. A total of over 2 hundreds of suspected MPS affected lung tissue samples were collected all over the country, from which 10 samples having typical Mhp infection and no obvious other pathogenic infections were screened out, and lyophilized and stored as virulent MPS tissular strains. Also, the tests of disease development upon challenge and attenuation by serial subculture were conducted in animals.

The selected 10 virulent tissular strains were inoculated to healthy and susceptible pigs of local variety by nasal drip, and after challenge, the test animals were observed to have clinical symptoms of MPS such as cough, shortness of breath, asarcia, and dog sitting, and typical shrimp meat like consolidation was found in the apical and cardiac lobes of the lungs of the animals after necropsy. 3 strains that have the most potent virulence and the highest immunogenicity were selected from the 10 virulent tissular strains for subculture, according to the latency prior to attack, the clinical symptoms, the incidence rate, the severity of the disease, and the titer of the haemagglutination antibody of the challenged animals.

Attenuation by Subculture:

The virulent tissular strains were inoculated to healthy newborn rabbits by intrapulmonary injection. The lung tissues of challenged rabbits were collected, homogenized, and then inoculated to healthy newborn rabbits. The subculture was conducted as such. Only 1 of the 3 virulent strains was successful in subculture in rabbits. During the subculture of the strain, a parallel subculture group was additionally set respectively at Generations 20, 40, 60, and 80, and the strain was serially subcultured 100 generations.

Mhp was isolated from the generation 100 lung tissue of the newborn rabbits by "affected lung block immersion method". Specifically, the animals were sacrificed by bleeding, the lung tissue was aseptically removed, cut into small blocks with a size of ½ sesame, washed with Hank's solution, and immersed in KM2 medium. Antibiotics were added, and incubation was continued at 37° C. The change in pH and the turbidity were observed every day. When the pH had an obvious change (dropped to 7.0-6.8) and homogenous turbidity was formed (at about 48 hrs), the culture was serially subcultured 4-5 generations by inoculating at a ratio of 1:5, and then subcultured by inoculating at a ratio of 1:10. After staining following Gurr's modified Giemsa staining method and examination under oil immersion microscope, the isolated microorganism was found to have a polymorphic mycelium, and have the typical morphological features of Mhp, and identified to be Mhp by particle agglutination reaction and metabolism inhibition test with standard Mhp positive serum. The isolated Mhp was purified by three times of solid cloning, identified again, lyophilized and stored.

The lyophilized and stored Mhp strain of generation F100 was revived, and continuously attenuated by serially subculturing in KM2 medium by inoculating at a ratio of 1:10. The strain was identified by PCR every five generations, and lyophilized and stored every 20 generations. The strain of generations F100, F140, F180, F220, F240, F280, and F320 was additionally subcultured different generations.

TABLE 1

Preliminary screening of attenuated strains

| Strain | Generation | Growth during in-vitro culture | Disease development of challenged animals | Remark |
|---|---|---|---|---|
| AN301 | F240 | Grow well, $10^9$ CCU/mL | No apparent lesion and no pathological changes | |
| AN302 | F110 | Grow slowly, $10^2$ CCU/mL | — | Loss in subculture in medium |
| AN303 | F280 | Grow well, $10^8$ CCU/mL | No apparent lesion and no pathological changes | |
| AN304 | F240 | Grow well, $10^7$ CCU/mL | No apparent lesion and no pathological changes | |
| AN305 | F32 | — | — | Loss in subculture in newborn rabbits |
| AN306 | F280 | Grow well, $10^9$ CCU/mL | No apparent lesion and no pathological changes | |
| AN307 | F140 | Grow well, $10^8$ CCU/mL | No apparent lesion and mild inflammatory pathological changes | |
| AN308 | F300 | Grow well, $10^9$ CCU/mL | No apparent lesion and no pathological changes | |
| AN309 | F360 | Grow well, $10^8$ CCU/mL | No apparent lesion and no pathological changes | |
| AN310 | F12 | — | — | Loss in subculture in newborn rabbits |

TABLE 1-continued

Preliminary screening of attenuated strains

| Strain | Generation | Growth during in-vitro culture | Disease development of challenged animals | Remark |
|---|---|---|---|---|
| AN311 | F260 | Grow slowly, $10^4$ CCU/mL | No apparent lesion and no pathological changes | |
| AN312 | F64 | — | — | Loss in subculture in newborn rabbits |

The various strains subjected to subculture was comprehensively analyzed in terms of subculture and growth abilities, and virulence, and 5 strains AN301, AN303, AN306, AN308, AN309 that grow rapidly, and have high titer and attenuated virulence were selected for the following virulence recovery test and immunoprotection assay.

Virulence Recovery Test of Attenuated Strain:

The screened strains were subjected to consecutive five-generation virulence recovery test. 3 mL of $10^8$ CCU/mL Mhp culture was injected to the tracheas of 3 healthy pigs. The animals were isolated and raised for 28 days, subjected to necropsy to observe whether lesions occur to the lungs of the test pigs, and pathologically sectioned to observe whether inflammatory changes occur. The apical and cardiac lobes and 5-7 g anterior portion of the diaphragm of the lung were aseptically removed, chopped, and ground into a paste. 100 mL of Hank's solution containing 1000 IU/mL penicillin was added, to formulate a 50 g/L lung suspension. The supernatant was aspirated and inoculated to 3 healthy pigs in an amount of 3 mL/pig on the same day. The strain was subcultured 5 generations as such, to observe whether virulence recovery takes places.

TABLE 2

Screening of attenuated strains by virulence recovery test

| | Strain | | | | |
|---|---|---|---|---|---|
| Generation | AN301 F240 | AN303 F280 | AN306 F280 | AN308 F300 | AN309 F360 |
| $1^{st}$ test | 0/3 | 0/3 | 0/3 | 0/3 | 0/3 |
| $2^{nd}$ test | 0/3 | 0/3 | 0/3 | 0/3 | 0/3 |
| $3^{rd}$ test | 0/3 | 0/3 | 0/3 | 0/3 | 0/3 |
| $4^{th}$ test | 1/3 | 0/3 | 0/3 | 0/3 | 0/3 |
| $5^{th}$ test | 2/3 | 0/3 | 0/3 | 0/3 | 0/3 |

The results show that the strain AN301 leads to inflammatory pathological changes of the lung of the animals at the fourth and fifth generations; and no obvious clinical symptoms of MPS are observed for the animals experiencing 5 inoculations of the remaining 4 strains, no consolidation of the lung is found after necropsy, and no inflammatory pathological changes such as lymphadenosis and lymphocyte and macrophage infiltration are found through pathological section examination, suggesting that the 4 strains subcultured are attenuated strains and have no virulence recovery ability.

Immunoassay of Attenuated Strains:

The screened strains were determined for immunogenicity and assayed for immunoprotection after challenge. Lyophilized strains were prepared and determined for the titer. The lyophilized strain was dissolved in a sterile phosphate buffer, and adjusted with the sterile phosphate buffer to have the same concentrations for test.

Immunoprotection after challenge was assayed in healthy and negative Meishan pigs at an age of 5-7 days. The animals were grouped at random, each group having 5 animals. The animals in the immunization group was inoculated with 0.5 mL of attenuated strain ($10^5$ CCU/pig) by intrapulmonary injection, and challenged by intratracheal injection with virulent Mhp strain 8 weeks after immunization, and subjected to necropsy 28 days later. A healthy control group and a challenged control group were additionally set.

The serum antibody was detected by indirect hemagglutination test. 1:10"++" or above is determined to be positive.

Score at necropsy: The animals were sacrificed 28 days after challenge, and the damage to the lung of the test pigs was scored following the method reported by MADEC and KOBISCH (1982). The whole lung includes a left cardiac lobe (LCL), a left apical lobe (LAL), a left diaphragmatic lobe (LDL), a right cardiac lobe (RCL), a right apical lobe (RAL), a right diaphragmatic lobe (RDL), and an accessory lobe (IL), and there are 7 lobes in total. The damage score of the lung is a sum of the damage scores for the dorsal surface and the ventral surface of the 7 lobes, and the total score is 28. Each lobe is scored 0-4 according to the injured area, where no damage is scored 0, 1-25% of area being damaged is scored 1, 26-50% of area being damaged is scored 2, 51-75% of area being damaged is scored 3, and 76-100% of area being damaged is scored 4.

TABLE 3

Screening of attenuated strain by immunoassay

| | Healthy control | Strain for immunization | | | | Challenged control |
|---|---|---|---|---|---|---|
| | | AN303 | AN306 | AN308 | AN309 | |
| | | Generation | | | | |
| | | F280 | F280 | F300 | F360 | |
| Antibody | − | − | + | + | − | − |
| Score for lesions of lung of pigs | 0.24 ± 0.15 | 6.23 ± 3.39 | 3.01 ± 1.45 | 7.73 ± 4.38 | 11.10 ± 6.77 | 20.29 ± 5.42 |

It can be known from analysis of the results that the attenuated strain AN306 has a high immunogenicity, and a high protection effect as confirmed by the challenge test. Moreover, the test shows that the strain grows rapidly when cultured in vitro, and has a high titer and a high safety. Therefore, the strain AN306 is selected and used as the live vaccine strain, and the primary generation is F280.

Example 2: Culture of Attenuated Mhp Strain AN306

Preparation of KM2 liquid medium (2050 mL): 1000 mL of Eagles medium, 10 g of hydrolyzed milk protein, 400 mL of swine serum, 20 mL of fresh yeast extract, 600 mL of Dulbecco phosphate buffer, 4,000,000 units of penicillin, and 3.5 mL of 0.4% phenol red, pH 7.4 7.6 (adjusted with 10 g/L NaOH).

1 vial of lyophilized attenuated Mhp strain AN306 was dissolved in 0.5 mL medium, and then 0.5 mL was inoculated in 4.5 mL medium, and incubated in a closed penicillin bottle at 37° C. When the color of the medium was changed from red to yellow, the culture was harvested in time, and inoculated into a fresh medium at a volume ratio of 1:10 for expansion culture. When the color of the medium was changed from red to yellow, the culture was harvested in time. Following this process, the strain was expansion cultured to 5000 mL and the culture was collected.

A lyoprotectant was formulated, which comprised 1.5 g of gelatine, 12.5 g of sucrose, 100 mL of double distilled water, and was sterilized in an autoclave for 15 min at 115° C., and adjusted to pH 7.0 with sterilized 1% NaOH. The culture was harvested and determined for the CCU level. The culture to be inoculated was added with the sterilized lyoprotectant at a volume ratio of 3:2, mixed fully, and packaged in ampoules in an amount of 0.5 mL/ampoule. The ampoule with packaged culture therein was placed in a lyophilizer, and lyophilized. After lyophilization, the bottle was sealed with nitrogen, and stored at −40° C. 1 mL culture was removed for DNA extraction and identification by PCR.

The culture of the attenuated strain AN306 thus obtained has a titer up to $10^9$ CCU/mL, and a production at liter level.

Example 3: Evaluation of Immunoprotection of Attenuated Live Vaccine Strain AN306 Against MPS Inoculated by Intrapulmonary Injection, and Comparison with Other Commercial Live and Inactivated Vaccines Preparation of Vaccines:

Lyophilized attenuated live vaccine strain AN306 against MPS was dissolved in a sterile phosphate buffer, to formulate a vaccine solution in which the live vaccine has a titer of $2\times10^5$ CCU/mL. Each animal was dosed 0.5 mL by intrapulmonary injection, that is, $10^5$ CCU/animal.

Commercial live vaccines: In this test, the only two live vaccines against MPS available in the market were used as control live vaccines, that is, (1) the live vaccine against MPS manufactured by Jilin Zhengye Biological Products Co., Ltd, which is chick embryo yolk sac tissue containing lapinized attenuated Mhp strain, referred to as Commercial vaccine 1 hereinafter, and used following the operations described in the instruction of the vaccine; and (2) Zhibining (trade name), which is a in-vitro culture of attenuated Mhp strain 168, referred to as Commercial vaccine 2 hereinafter, and used following the operations described in the instruction of the vaccine.

Commercial inactivated vaccine: In this test, two inactivated vaccines against MPS currently widely available in the market were used as control inactivated vaccines, that is (1) RespiSure (trade name), which is referred to as Commercial vaccine 3 hereinafter, and used following the operations described in the instruction of the vaccine; and (2) MycoFLEX (trade name), which is referred to as Commercial vaccine 4 hereinafter, and used following the operations described in the instruction of the vaccine.

Immunization and Challenge of Animals:

70 healthy piglets were assigned to 7 groups at random, where Group G1 is a healthy control group, which is not immunized and challenged; Group G7 is a challenged control group, which is not immunized, but challenged; and Groups G2-G6 are groups with immunization of vaccines. The specific grouping and immunization method was as shown in a table below. The animals were immunized and then challenged. 8 weeks after immunization, the animals in Groups G2-G7 were challenged by intratracheal injection with virulent Mhp strain, and subjected to necropsy 28 days later.

The test was the experiments were done in duplicate with two varieties including Suzhong pig and Topigs.

Result:

The MPS lesion in the lung of the animals was scored following the method described in Example 1. The result shows that the animals immunized with attenuated live vaccine strain AN306 against MPS have obviously lessened lesions in the lung, and the statistical difference is highly significant ($P<0.01$) compared with the challenged control group (by One-way ANOVA). The average disease index is obviously lower than that of the commercial live and inactivated vaccines (Commercial vaccine 1, $P<0.01$; Commercial vaccine 2, $P<0.05$; Commercial vaccine 3, $P<0.01$; and Commercial vaccine 4, $P<0.01$) currently widely available in the market, suggesting that the attenuated live vaccine strain AN306 can help the immunized animals to resist Mhp infection effectively, with a protection being superior to that of the vaccines widely available in the market.

TABLE 4

Evaluation of immunoprotection of attenuated live vaccine strain AN306 against MPS inoculated by intrapulmonary injection, and comparison with other commercial live and inactivated vaccines

| | Group No. | | | | | | |
| --- | --- | --- | --- | --- | --- | --- | --- |
| | G1 | G2 | G3 | G4 | G5 | G6 | G7 |
| Group division | Healthy control group | Live vaccine group | Commercial vaccine 1 | Commercial vaccine 2 | Commercial vaccine 3 | Commercial vaccine 4 | Challenged control group |
| Route of immunization | — | Intrapulmonary injection | Intrathoracic injection | Intrapulmonary injection | Intramuscular injection | Intramuscular injection | — |
| Score of lesions of the lung (test 1) | 0.50 ± 0.71 | 2.60 ± 0.84 | 5.00 ± 1.15 | 3.80 ± 1.14 | 10.60 ± 2.37 | 11.90 ± 3.41 | 21.90 ± 2.02 |

TABLE 4-continued

Evaluation of immunoprotection of attenuated live vaccine strain AN306 against MPS inoculated by intrapulmonary injection, and comparison with other commercial live and inactivated vaccines

| | Group No. | | | | | | |
|---|---|---|---|---|---|---|---|
| | G1 | G2 | G3 | G4 | G5 | G6 | G7 |
| Score of lesions of the lung (test 2) | 0.40 ± 0.70 | 2.80 ± 1.40 | 5.10 ± 2.18 | 4.00 ± 1.25 | 8.30 ± 2.41 | 6.00 ± 2.17 | 17.90 ± 3.21 |

Example 4: Evaluation of Immunoprotection of Attenuated Live Vaccine Strain AN306 Against MPS Inoculated by Aerosol Immunization Preparation of Vaccine Diluent:

Sterilized 5%-10% glycerol solution in deionized water, pH 6.8-7.5.

Formulation of Vaccines:

Lyophilized attenuated live vaccine strain AN306 against MPS was dissolved in the vaccine diluent, to formulate a vaccine solution in which the live vaccine has a titer of $10^6$ CCU/mL.

Immunization and Challenge of Animals:

40 healthy and negative Topigs at an age of 5-7 days were assigned to 4 groups at random, where Group G1 is a healthy control group, which is not immunized and challenged; Group G2 is a group with aerosol immunizations of live vaccine strain AN306 in an amount of 0.5 mL ($5\times10^5$ CCU/animal), in which 2 weeks after the first immunization, the immunization is conducted again, followed by challenge; Group G3 is a commercial vaccine group, in which the commercial inactivated vaccine RespiSure against MPS currently widely available in the market is inoculated, the operation is following the instruction of the vaccine, and challenge is performed after immunization; and Group G4 is a challenged control group, which is not immunized, but challenged. The animals in Groups G2, G3, and G4 were challenged by intratracheal injection with virulent Mhp strain 8 weeks after the first immunization, and subjected to necropsy 28 days later.

Result:

The MPS lesion in the lung of the animals was scored following the method described in Example 1, specifically as shown in a table below. The result shows that the animals with aerosol immunization of attenuated live vaccine strain AN306 against MPS have obviously lessened lesions in the lung, the statistical difference is highly significant (P<0.01) compared with the challenged control group, and the lesions are obviously reduced compared with the case in which the commercial inactivated vaccine is inoculated (P<0.01), suggesting that the attenuated live vaccine strain can help the immunized animals to resist Mhp infection through aerosol immunization, with a protection being superior to that of the inactivated vaccine widely available in the market.

TABLE 5

Evaluation of immunoprotection of attenuated live vaccine strain AN306 against MPS inoculated by aerosol immunization

| | Group Division | | | |
|---|---|---|---|---|
| | G1 Healthy control group | G2 Live vaccine group | G3 Commercial inactivated vaccine group | G4 Challenged control group |
| Score of lesions of the lung | 1.08 ± 0.27 | 3.83 ± 2.48 | 8.25 ± 4.14 | 20.34 ± 3.45 |

Example 5: Evaluation of Immunoprotection of Attenuated Live Vaccine Strain AN306 Against MPS Inoculated by Intramuscular Injection Preparation of Vaccines:

Lyophilized attenuated live vaccine strain AN306 against MPS was used. The adjuvant used was a mixed adjuvant of 5 mg/mL carbomers and 30 mg/mL *Astragalus* polysaccharides formulated in a sterile phosphate buffer. The lyophilized vaccine strain was dissolved in the adjuvant solution, to formulate a vaccine solution in which the live vaccine has a titer of $2.5\times10^5$ CCU/mL.

Immunization and Challenge of Animals:

40 healthy and negative Suzhong pigs at an age of 5-7 days were assigned to 4 groups at random, where Group G1 is a healthy control group, which is not immunized and challenged; Group G2 is a group immunized with a live vaccine by intramuscular injection in an amount of 2 mL ($5\times10^5$ CCU/animal), in which 2 weeks after the first immunization, the immunization is conducted again, followed by challenge; Group G3 is a commercial vaccine group, in which the commercial inactivated vaccine RespiSure against MPS currently widely available in the market is inoculated, the operation is following the instruction of the vaccine, and challenge is performed after immunization; and Group G4 a challenged control group, which is not immunized, but challenged. The animals in Groups G2, G3, and G4 were challenged by intratracheal injection with virulent Mhp strain 8 weeks after the first immunization, and subjected to necropsy 28 days later.

Result:

The MPS lesion in the lung of the animals was scored following the method described in Example 1, specifically as shown in a table below. The result shows that the animals immunized with attenuated live vaccine strain AN306 against MPS by intramuscular injection have obviously lessened lesions in the lung, the statistical difference is highly significant (P<0.01) compared with the challenged control group, and the lesions are obviously reduced compared with the case in which the commercial inactivated vaccine is inoculated (P<0.01), suggesting that the attenuated live vaccine strain can help the immunized animals to resist Mhp infection through intramuscular injection, with a protection being superior to that of the inactivated vaccine widely available in the market.

TABLE 6

Evaluation of immunoprotection of attenuated live vaccine strain AN306 against MPS inoculated by intramuscular injection

| | Group Division | | | |
|---|---|---|---|---|
| | G1 Healthy control group | G2 Live vaccine group | G3 Commercial inactivated vaccine group | G4 Challenged control group |
| Score of lesions of the lung | 0.98 ± 0.43 | 4.57 ± 2.32 | 7.88 ± 4.78 | 20.65 ± 7.51 |

Example 6: Evaluation of Immunoprotection of Attenuated Live Vaccine Strain AN306 Against MPS Inoculated by Nasal Immunization Preparation of Vaccines:

Fresh culture of Mhp strain AN306 having a titer of $5 \times 10^6$ CCU/mL was used. A vaccine containing chitosan as an adjuvant was prepared as follows. Chitosan was dissolved in a 1% acetic acid solution, to formulate a stock solution containing 1% chitosan, which was adjusted to pH 6.5 with a 0.1 M NaOH solution. The stock solution containing chitosan was diluted with 0.1 M NaAc—HAc (pH 6.5) solution to give a final concentration of chitosan of 0.2%. The fresh culture of the Mhp strain AN306 was concentrated at 12000 rpm for 30 min, to collect the pellet, which was resuspended in 1 mL of 50 mM $Na_2SO_4$, to give a titer of $6.66 \times 10^6$ CCU/mL. 5 mL of 0.2% chitosan solution was added with 1 mL of the $Na_2SO_4$ solution containing Mhp, and mixed by stirring. 660 µL of sodium tripolyphosphate (4 mg/mL) solution was added slowly with stirring, to obtain a cream white homogeneous suspension.

Immunization and Challenge of Animals:

32 healthy and negative Topigs at an age of 5-7 days were assigned to 4 groups at random, where Group G1 is a healthy control group, which is not immunized and challenged; Group G2 is a group with nasal immunizations of live vaccine strain AN306 in an amount of 0.5 mL ($5 \times 10^5$ CCU/animal), in which 2 weeks after the first immunization, the immunization is conducted again, followed by challenge; Group G3 is a commercial vaccine group, in which the commercial inactivated vaccine RespiSure against MPS currently widely available in the market is inoculated, the operation is following the instruction of the vaccine, and challenge is performed after immunization; and Group G4 is a challenged control group, which is not immunized, but challenged. The animals in Groups G2, G3, and G4 were challenged by intratracheal injection with virulent Mhp strain 8 weeks after the first immunization, and subjected to necropsy 28 days later.

Result:

The MPS lesion in the lung of the animals was scored following the method described in Example 1, specifically as shown in a table below. The result shows that the animals immunized with attenuated live vaccine strain AN306 against MPS have obviously lessened lesions in the lung, the statistical difference is highly significant (P<0.01) compared with the challenged control group, and the lesions are obviously reduced compared with the case in which the commercial inactivated vaccine is inoculated (P<0.01), suggesting that the attenuated live vaccine strain can help the immunized animals to resist Mhp infection through nasal immunization, with a protection being superior to that of the inactivated vaccine widely available in the market.

TABLE 7

Evaluation of immunoprotection of attenuated live vaccine strain AN306 against MPS inoculated by nasal immunization

| | Group division | | | |
|---|---|---|---|---|
| | G1 Healthy control group | G2 Live vaccine group | G3 Commercial inactivated vaccine group | G4 Challenged control group |
| Score of lesions of the lung | 0.21 ± 0.18 | 3.03 ± 2.68 | 8.72 ± 4.19 | 22.68 ± 4.67 |

Example 7: Evaluation of Immunoprotection of Divalent Vaccine of Attenuated Live Vaccine Strain AN306 Against MPS and Inactivated HPS Vaccine Preparation of Vaccines:

Fresh culture of Mhp strain AN306 having a titer of $1 \times 10^6$ CCU/mL was used.

Fresh culture of HPS strain XX0306 serotype 5 (which is isolated by Veterinary Research Institute, Jiangsu Academy of Agricultural Sciences, has a good immunogenicity, and is proved through tests to be suitable for the preparation of inactivated vaccines of HPS, with the protection effect being good) was inactivated for 12 hrs with a formaldehyde solution having a final concentration of 0.2% after viable count. Then the inactivation was terminated by adding 0.2% sodium metabisulfite. The cells were concentrated to $1 \times 10^{10}$ CFU/mL.

The adjuvant used was a mixed adjuvant of 5 mg/mL carbomers and immunostimulating complex matrix (containing QuilA 500 µg/mL, cholesterol 100 µg/mL, and phospholipid 100 µg/mL) formulated in a sterile phosphate buffer.

0.5 mL of fresh Mhp culture was mixed fully with 0.5 mL of inactivated HPS strain XX0306 serotype 5 and the adjuvant at a ratio of 1:1:2, with which the animals were immunized.

Immunization and Challenge of Animals:

30 healthy and negative Suzhong pigs at an age of about 10 days were assigned to 4 groups at random, where Group G1 is a healthy control group having 10 animals, which is not immunized and challenged, and in which 5 of 10 animals are subjected to necropsy at the same time with the animals in Groups G2 and G3, and the other 5 animals are subjected to necropsy at the same time with the animals in Groups G4 and G5; Group G2 is a group having 5 animals and immunized with the bivalent vaccine and challenged with Mhp, where the immunization is performed by intramuscular injection of 2 mL of the prepared bivalent vaccine (AN306 live vaccine: $2.5 \times 10^5$ CCU/mL, inactivated HPS strain XX0306 serotype 5: $2.5 \times 10^9$ CFU/mL), immunization is performed again 3 weeks after the first immunization, and challenge with virulent Mhp is conducted by intratracheal injection 8 weeks after the first immunization; Group G3 is a control group challenged with Mhp and having 5 animals, which is not immunized, but challenged in the same way as that for the animals in Group G2; Group G4 is a group having 5 animals and immunized with the bivalent vaccine and challenged with HPS, where the immunization is performed by intramuscular injection of 2 mL of the prepared bivalent vaccine (AN306 live vaccine: $2.5 \times 10^5$ CCU/mL, inactivated HPS strain XX0306 serotype 5: $2.5 \times 10^9$ CFU/mL), immunization is performed again 3 weeks after the first immunization, and challenge with virulent HPS is conducted by intraperitoneal injection 6 weeks after the first immunization; and Group G5 is a control group having 5 animals and challenged with HPS, which is not immunized, but challenged in the same way as that for the animals in Group G4.

Result:

(1) Protection Against Mhp Infection

The animals were subjected to necropsy 28 days after challenge, and the MPS lesion in the lung of the animals was scored following the method described in Example 1. The results are shown in a table below and suggest that after immunization with the bivalent vaccine, the lesion in the lung is obviously lessened (P<0.01).

(2) Protection Against HPS Infection

The clinical symptoms of HPS infection include reduced appetite, roughened hair coats, ear and body skin flushing, increased nasal discharge, and respiratory distress, swelling joint, and failure to stand occurring in a later stage. At necropsy, pleural effusion, abdominal effusion, different degrees of pleural and peritoneal adhesion, swelling joint, increased mucus in articular cavity, bleeding lung, lymph node enlargement and other physiological changes may be found. The disease status of HPS infection in the animals in each group was determined based on the above criteria, and outlined in a table below. The results suggest that after immunization with the bivalent vaccine, the incidence of HPS infection in the animals are obviously lessened ($P<0.01$).

nization is performed again 2 weeks after the first immunization, and challenge with virulent Mhp is conducted by intratracheal injection 8 weeks after the first immunization; Group G3 is a control group challenged with Mhp and having 5 animals, which is not immunized, but challenged in the same way as that for the animals in Group G2; Group G4 is a group having 5 animals and immunized with the bivalent vaccine and challenged with PRRSV, where the immunization is performed by intramuscular injection of 2 mL of the prepared bivalent vaccine, immunization is performed again

TABLE 8

Evaluation of immunoprotection of divalent vaccine of attenuated live vaccine strain AN306 against MPS and inactivated HPS Live vaccine

| | Group division | | | | |
|---|---|---|---|---|---|
| | G1 Healthy control group | G2 Group immunized with the bivalent vaccine and challenged with Mhp | G3 Control group challenged with Mhp | G4 Group immunized with the bivalent vaccine and challenged with HPS | G5 Control group challenged with HPS |
| Immunization | Not immunized | Immunized with the bivalent vaccine | Not immunized | Immunized with the bivalent vaccine | Not immunized |
| Challenge with Mhp | Not challenged | Challenged | Challenged | Not challenged | Not challenged |
| Challenge with HPS | Not challenged | Not challenged | Not challenged | Challenged | Challenged |
| Score of MPS lesion | 0.54 ± 0.28 | 5.37 ± 4.36 | 19.81 ± 6.57 | Not evaluated | Not evaluated |
| Evaluation of disease status of HPS infection | 0/5 | Not evaluated | Not evaluated | 1/5 | 5/5 |

Example 8: Evaluation of Immunoprotection of Divalent Vaccine of Attenuated Live Vaccine Strain AN306 Against MPS and Live PRRSV Vaccine Preparation of Vaccines:

A mixed adjuvant containing 10 mg/mL chitosan and 10 mg/mL levamisole was formulated in a sterile phosphate buffer. Lyophilized live vaccine strain AN306 against MPS was dissolved in 1.5 mL adjuvant, to obtain a live vaccine against MPS as a solution having a specification of 1 dose ($5\times10^5$ CCU)/1.5 mL.

Commercial live PRRSV vaccine (strain ATCCVR-2332) was dissolved in saline, to obtain a live PRRSV vaccine as a solution having a specification of 2 dose/mL.

The two vaccine solutions were mixed at a ratio (by volume) of 3:1, with which the animals were immunized by inoculating 2 mL per animal, that is, 1 dose of the live vaccine against MPS and 1 dose of the live PRRSV vaccine.

Immunization and Challenge of Animals:

30 healthy and negative Suzhong pigs at an age of about 10 days were assigned to 4 groups at random, where Group G1 is a healthy control group having 10 animals, which is not immunized and challenged, and in which 5 of 10 animals are subjected to necropsy at the same time with the animals in Groups G2 and G3, and the other 5 animals are subjected to necropsy at the same time with the animals in Groups G4 and G5; Group G2 is a group having 5 animals and immunized with the bivalent vaccine and challenged with Mhp, where the immunization is performed by intramuscular injection of 2 mL of the prepared bivalent vaccine, immu- 2 weeks after the first immunization, and challenge with virulent PRRSV is conducted by intraperitoneal injection at the neck 6 weeks after the first immunization; and Group G5 is a control group having 5 animals and challenged with PRRSV, which is not immunized, but challenged in the same way as that for the animals in Group G4.

Result:

(1) Protection Against Mhp Infection

The animals were subjected to necropsy 28 days after challenge, and the MPS lesion in the lung of the animals was scored following the method described in Example 1. The results are shown in a table below and suggest that after immunization with the bivalent vaccine, the lesion in the lung is obviously lessened ($P<0.01$).

(2) Protection Against PRRSV Infection

After challenge, the animals were observed and detected for the body temperature every day. The criteria for determining the attack of PRRSV infection include consecutive 3 or more days of high fever of 41° C. or higher, lassitude, reduced appetite, occurrence of conjunctivitis and respiratory symptoms such as cough and shortness of breath, death, and lamellar consolidation of the lung at necropsy. The results show that the animals in the control group challenged with PRRSV all suffer from the disease, and two of them are dead; and the animals in the group immunized with the bivalent vaccine have no obvious symptoms of the disease and all survive.

TABLE 9

Evaluation of immunoprotection of divalent vaccine of attenuated live vaccine strain AN306 against MPS and live PRRSV vaccine

| | Group division | | | | |
|---|---|---|---|---|---|
| | G1 Healthy control group | G2 Group immunized with the bivalent vaccine and challenged with Mhp | G3 Control group challenged with Mhp | G4 Group immunized with the bivalent vaccine and challenged with PRRSV | G5 Control group challenged with PRRSV |
| Immunization | Not immunized | Immunized with the bivalent vaccine | Not immunized | Immunized with the bivalent vaccine | Not immunized |
| Challenge with Mhp | Not challenged | Challenged | Challenged | Not challenged | Not challenged |
| Challenge with PRRSV | Not challenged | Not challenged | Not challenged | Challenged | Challenged |
| Score of MPS lesion | 0.22 ± 0.15 | 5.05 ± 3.89 | 23.24 ± 3.72 | Not evaluated | Not evaluated |
| Evaluation of disease status of PRRS | 0/5 | Not evaluated | Not evaluated | 0/5 | 5/5 |

What is claimed is:

1. An attenuated *Mycoplasma hyopneumoniae* (Mhp) strain AN306, which is deposited in China Center for Type Culture Collection (CCTCC) with an accession number: CCTCC NO. M2012431.

2. A method comprising:
administering an effective amount of the attenuated Mhp strain AN306 according to claim 1 to a pig in order to treat an Mhp infection.

3. An immunogenic composition against mycoplasmal pneumonia of swine (MPS), comprising the attenuated Mhp strain AN306 according to claim 1.

4. The immunogenic composition against MPS according to claim 3, further comprising a pharmaceutically acceptable carrier or excipient.

5. The immunogenic composition against MPS according to claim 3, further comprising an immunization adjuvant.

6. The immunogenic composition against MPS according to claim 3, further comprising an immunogen of an additional pathogen.

7. The immunogenic composition against MPS according to claim 6, wherein the additional pathogen includes at least one of viruses, bacteria, fungi, and parasites.

8. The immunogenic composition against MPS according to claim 7, wherein the additional pathogen is porcine circovirus, *Haemophilus parasuis*, porcine reproductive and respiratory syndrome virus, *Mycoplasma hyorhinis*, *Mycoplasma hyosynoviae*, or swine influenza virus.

9. The immunogenic composition against MPS according to claim 3, wherein the vaccine is in the form of an intrapulmonary injectable formulation, an intramuscular injectable formulation, an aerosol, an oral formulation, or a nasal drop.

10. A method for preparing the immunogenic composition against MPS according to claim 3, comprising combining an effective amount of the Mhp strain AN306 with a pharmaceutically acceptable carrier or excipient, an immunization adjuvant, and an immunogen of an additional pathogen.

11. The method according to claim 2, wherein the effective amount of the attenuated Mhp strain AN306 is administered in the form of an intrapulmonary injectable formulation, an intramuscular injectable formulation, an aerosol, an oral formulation, or a nasal drop.

* * * * *